US008029545B2

(12) United States Patent
Graf et al.

(10) Patent No.: US 8,029,545 B2
(45) Date of Patent: Oct. 4, 2011

(54) ARTICULATING CONNECTING MEMBER AND ANCHOR SYSTEMS FOR SPINAL STABILIZATION

(75) Inventors: Henry Graf, Tassin la Demi-Lune (FR); Stephan Chojnicki, Villepinte (FR); Roy Lim, Germantown, TN (US)

(73) Assignee: Warsaw Orthopedic Inc., Warsaw, IN (US)

( * ) Notice: Subject to any disclaimer, the term of this patent is extended or adjusted under 35 U.S.C. 154(b) by 1127 days.

(21) Appl. No.: 11/348,687

(22) Filed: Feb. 7, 2006

(65) Prior Publication Data

US 2007/0198014 A1 Aug. 23, 2007

(51) Int. Cl.
*A06B 17/70* (2006.01)

(52) U.S. Cl. ........................................ 606/256; 606/266

(58) Field of Classification Search .................. 606/253, 606/254, 259, 266, 267, 305, 310, 306, 246–252, 606/255–258, 260–265, 268–279, 300–304, 606/307–309, 311–331; 403/76, 77, 133, 403/135

See application file for complete search history.

(56) References Cited

U.S. PATENT DOCUMENTS 1,842,747 A * 1/1932 Crawford et al. ............. 403/135
3,097,005 A * 7/1963 Fickler .............................. 403/6
5,375,823 A 12/1994 Navas
5,415,653 A * 5/1995 Wardle et al. ..................... 606/7
5,480,401 A 1/1996 Navas
5,486,174 A 1/1996 Fournet-Fayard et al.
5,540,688 A 7/1996 Navas
5,562,737 A 10/1996 Graf
5,569,247 A 10/1996 Morrison
5,628,740 A 5/1997 Mullane
5,669,911 A * 9/1997 Errico et al. .................. 606/264
5,690,630 A * 11/1997 Errico et al. .................. 606/264
5,735,851 A 4/1998 Errico et al.
5,755,796 A * 5/1998 Ibo et al. .................... 623/17.16
5,800,435 A 9/1998 Errico et al.
5,961,516 A 10/1999 Graf
6,010,504 A 1/2000 Rogozinski
6,063,089 A 5/2000 Errico et al.
6,086,588 A * 7/2000 Ameil et al. .................. 606/266
6,267,765 B1 7/2001 Taylor et al.
6,290,700 B1 9/2001 Schmotzer (Continued)

FOREIGN PATENT DOCUMENTS

DE 19950075 A1 * 4/2001

(Continued)

OTHER PUBLICATIONS

Definition of along. Dictionary.com. Retrieved Sep. 24, 2009.*

(Continued)

*Primary Examiner* — Eduardo C Robert
*Assistant Examiner* — Jerry Cumberledge

(57) ABSTRACT

Stabilization systems for stabilizing one or more vertebral levels are provided. The systems include anchors engageable to the vertebrae and an elongate connecting member system that maintains distraction between the vertebrae while allowing at least limited vertebral motion of the stabilized vertebral levels. The stabilization systems can be employed alone in non-fusion procedure or in conjunction interbody fusion and/or postero-lateral fusion procedures. The connecting members are structured to maintain a constant or slightly variable distance between the anchors to which the connecting members are connected while the connections of the connecting members with the anchors allow motion.

18 Claims, 8 Drawing Sheets

U.S. PATENT DOCUMENTS

| | | | | |
|---|---|---|---|---|
| 6,468,276 | B1 | 10/2002 | McKay | |
| 6,554,831 | B1 | 4/2003 | Rivard et al. | |
| 6,610,062 | B2 | 8/2003 | Bailey et al. | |
| 6,623,485 | B2 | 9/2003 | Doubler et al. | |
| 6,626,904 | B1 | 9/2003 | Jammet et al. | |
| 6,676,661 | B1 | 1/2004 | Benlloch et al. | |
| 6,682,529 | B2 * | 1/2004 | Stahurski | 606/301 |
| 6,755,830 | B2 | 6/2004 | Minfelde et al. | |
| 6,802,844 | B2 | 10/2004 | Ferree | |
| 2003/0055427 | A1 * | 3/2003 | Graf | 606/61 |
| 2003/0153912 | A1 | 8/2003 | Graf | |
| 2003/0163133 | A1 | 8/2003 | Altarac et al. | |
| 2004/0039384 | A1 | 2/2004 | Boehm, Jr. et al. | |
| 2004/0236329 | A1 | 11/2004 | Panjabi | |
| 2005/0049708 | A1 | 3/2005 | Atkinson et al. | |
| 2005/0113927 | A1 | 5/2005 | Malek | |
| 2005/0154393 | A1 * | 7/2005 | Doherty et al. | 606/73 |
| 2005/0192573 | A1 | 9/2005 | Abdelgany et al. | |
| 2005/0216005 | A1 | 9/2005 | Howland | |
| 2006/0052786 | A1 * | 3/2006 | Dant et al. | 606/61 |
| 2006/0058788 | A1 * | 3/2006 | Hammer et al. | 606/61 |
| 2006/0079899 | A1 * | 4/2006 | Ritland | 606/61 |
| 2006/0229609 | A1 | 10/2006 | Wang | |
| 2007/0093831 | A1 * | 4/2007 | Abdelgany et al. | 606/61 |

FOREIGN PATENT DOCUMENTS

| | | | |
|---|---|---|---|
| EP | 0 612 507 | A1 | 8/1994 |
| EP | 0 654 249 | A1 | 5/1995 |
| WO | WO 98/55038 | | 12/1998 |
| WO | WO 02/00141 | A1 | 1/2002 |
| WO | WO 02/076315 | A1 | 10/2002 |
| WO | WO 03/026523 | A1 | 4/2003 |
| WO | WO 2005023125 | A1 * | 3/2005 |

OTHER PUBLICATIONS

Definition of with. Dictionary.com. Retrieved Sep. 24, 2009.*

* cited by examiner

ARTICULATING CONNECTING MEMBER AND ANCHOR SYSTEMS FOR SPINAL STABILIZATION

BACKGROUND

Various types of devices and systems have been used to stabilize portions of bones including the spine. Spinal stabilization techniques have employed plating and connecting members on the posterior, anterior, lateral, postero-lateral and antero-lateral portions of a spinal column segment. Such systems can provide rigid or dynamic fixation of a spinal column segment for the repair of injured or diseased vertebrae, intervertebral discs, and other elements of the spinal column. There remains a need for dynamic stabilization systems that are adaptable for various stabilization requirements in a spinal procedure.

SUMMARY

Spinal stabilization systems are provided that include elongated connecting member systems positionable between at least two anchors. The connecting members systems and anchors are structured to articulate relative to one another to facilitate at least limited spinal motion of the stabilized vertebral level or levels. The connecting member systems can further be provided with rigid or semi-rigid body portions between the articulating connections to maintain distraction of the stabilized vertebral level.

According to one aspect, a system for stabilization of a spinal column segment comprises an elongated connecting member, a first anchor and a second anchor. The connecting member extends between a first end and a second end. The first end includes a ball-shaped member having a circumferential cut. A connecting portion extends from the first end to a second end. The second end includes an anchor engaging member defining a passage. The first anchor includes a distal bone engaging portion and a proximal head that defines a socket having a first maximum dimension and an opening into the socket having a second maximum dimension that is less than the first maximum dimension. The cut is sized to pass through the opening when aligned therewith and the ball-shaped member is sized greater than the second maximum dimension to prevent the ball-shaped member from passing through the opening of the socket when the cut is not aligned with the opening. The second anchor includes a distal bone engaging portion and a proximal portion including a stem extending proximally from the bone engaging portion that is pivotal relative thereto. The stem is positionable in the passage of the anchor engaging member of the connecting member to secure the connecting member thereto.

According to another aspect, a system for stabilization of a spinal column segment comprises first and second anchors each having a bone engaging portion and a cap pivotally coupled to a proximal end of the bone engaging portion, and a third anchor between the first and second anchors having a bone engaging portion extending along a longitudinal axis and a proximal portion defining a passage extending therethrough transversely to the longitudinal axis. The system further includes a connecting member assembly comprising a first connecting portion extending along an axis and having a first end coupled to the cap of the first anchor and a second end in the passage of the third anchor. The connecting member assembly also includes a second connecting portion extending along an axis and having a first end coupled to the cap of the second anchor and a second end pivotally coupled to the second end of the first connecting portion in the passage of the third anchor. When assembled the axes of the first and second connecting portions are generally aligned with one another in the passage.

According to a further aspect, an anchor for securing an elongated connecting member along a spinal column comprises a distal bone engaging portion extending along a longitudinal axis and a proximal head portion defining an internal socket and an opening in communication with the socket. The internal socket has a maximum dimension greater than a maximum dimension of the opening. The opening is located in a chamfered surface of the head that is formed at an acute angle to the longitudinal axis.

According to yet another aspect, a method for assembling a spinal stabilization system comprises: providing a first anchor including a bone engaging portion and a proximal head, the head defining a socket therein and an opening into the socket along a chamfered surface of the head; providing an elongated connecting member having a ball-shaped member at one end thereof, the ball-shaped member defining a circumferential cut extending therearound; aligning the circumferential cut with the opening into the socket; inserting the ball-shaped member through the opening and into the socket in the aligned orientation; and pivoting the ball-shaped member in the socket so that the cut is not aligned with the opening, wherein the ball-shaped member is sized to prevent the ball-shaped member from passing through the opening when the cut is not aligned with the opening.

According to another aspect, a method for assembling a spinal stabilization system construct comprises: providing a first anchor having a distal bone engaging portion and a proximal portion; providing a second anchor having a distal bone engaging portion and a proximal portion; providing a third anchor having a distal bone engaging portion extending along a longitudinal axis and a proximal portion defining a passage extending therethrough transversely to the axis; pivotally coupling a first end of a first connecting portion in the passage of the third anchor, the first end defining a socket opening transversely to the longitudinal axis; pivotally coupling a first end of a second connecting portion in the socket of the first connecting portion in the passage; pivotally coupling a second end of the first connecting portion to the proximal portion of the first anchor; and pivotally coupling a second end of the second connecting portion to the proximal portion of the second anchor.

Related features, aspects, embodiments, objects and advantages of the present invention will be apparent from the following description.

DESCRIPTION OF THE ILLUSTRATED EMBODIMENTS

Figure 1:
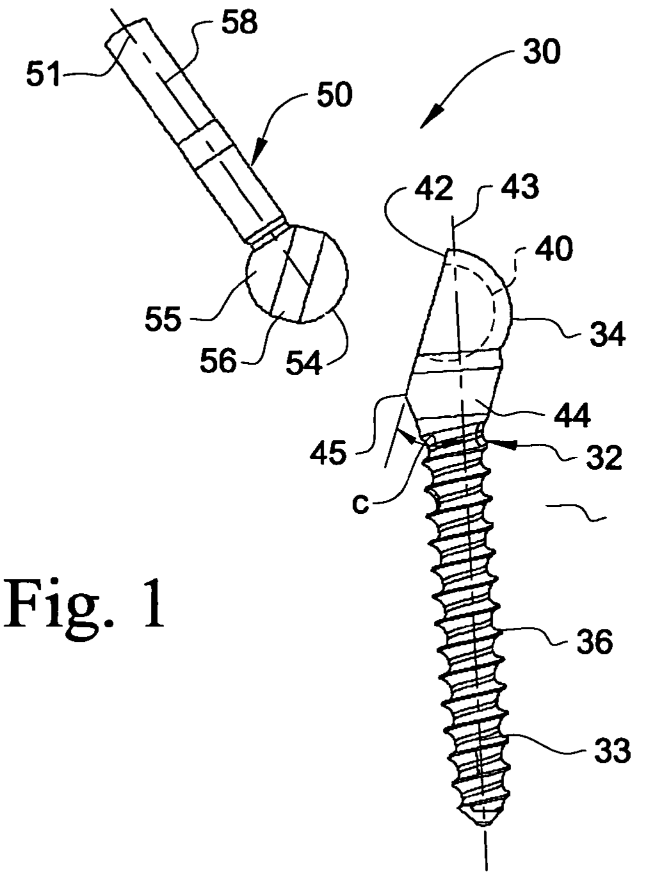
FIG. 1 is an exploded elevation view of one embodiment connecting member and anchor assembly.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Stabilization systems for stabilizing one or more vertebral levels are provided. The systems include anchors engageable to the vertebrae and a connecting member system that maintains distraction between the vertebrae while allowing at least limited vertebral motion of the stabilized vertebral levels. The stabilization systems can be employed alone in non-fusion procedure or in conjunction interbody fusion and/or posterolateral fusion procedures. The connecting member systems are structured to maintain a constant or slightly variable distance between the anchors to which the connecting member systems are connected while the connections of the connecting member systems with the anchors allow motion. Non-rigid connections between the connecting member systems and anchors may reduce the potential for anchor pullout from a vertebra.

Figure 2:
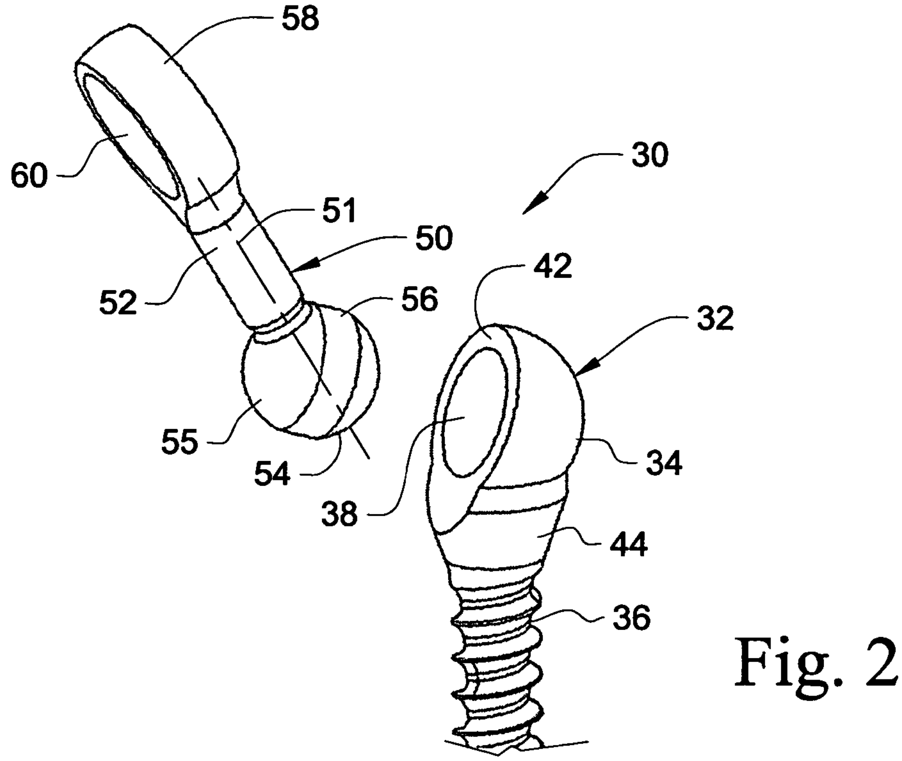
FIG. 2 is a perspective view of a portion of the exploded assembly of FIG. 1.

Referring now to FIG. 1, there is shown a stabilization system 30 that includes an anchor 32 and a connecting member 50. Anchor 32 includes a proximal head 34 and a distal bone engaging portion 36. As shown further in FIG. 2, head 34 includes bulbous shape with a chamfered side 42. Side 42 forms a planar surface extending about a side opening 38 that extends into a socket 40. Socket 40 includes a shape that forms a portion of a sphere within head 34. Anchor 32 further includes a distally tapered neck 44 between head 34 and bone engaging portion 36. Neck 44 includes a frusto-conical shape that is interrupted along a side thereof by chamfered side 42.

The location of chamfered side 42 relative to the spherically-shaped socket 40 provides socket 40 with a size that is greater than at least half a sphere. For example, as shown in FIG. 1, a proximal end of chamfered side 42 can start at a proximal location 43 aligned along longitudinal axis 33. Side 42 lies in a plane that extends distally from location 43 at an acute angle C relative to axis 33. In one embodiment, angle C is about 20 degrees. Other embodiments contemplate other angular ranges for angle C. Side 42 includes a distal end 45 offset to one side of axis 33 in neck 44. The portion of socket 40 on the opposite side of axis 33 forms half of a sphere or half of a spherical shape. Accordingly, socket 40 includes a size that is greater than half of a sphere or spherical shape, and the dimension of opening 38 is slightly less than the least dimension of socket 40.

Connecting member 50 includes an elongate body 52 extending along a longitudinal axis 51 between a first end 54 and a second end 58. Body 52 can be in the form of a rod, plate, or other suitable structure for extending between ends 54, 58. Second end 58 includes an engaging member defining a passage 60 to receive a second anchor therein. In the illustrated embodiment, second end 58 includes a ring-like shape with a central passage 60. Other embodiments contemplate other shapes for second end 58, including forked shapes, clamping arrangements, elongated connecting member-like shapes, and plate-like shapes, for example. Passage 60 can be circular, elongated, closed, open-ended, open-sided, constant, or variable in shape.

First end 54 includes a ball-shaped end member 55 having a circumferential cut 56 therearound. As used herein, ball-shaped may include shapes that form a sphere, are spherical, that include one or more planar surfaces, and/or that include one or more compound curvatures. End member 55 can include a diameter or maximum dimension that is sized and shaped with the diameter or maximum dimension of socket 40 to permit end member 55 to be received in and rotate in socket 40. Cut 56 can be formed radially about end member 55. Cut 56 reduces the maximum diameter or dimensions of end member 55 at the location of cut 56 to a diameter or dimension that corresponds to the size of opening 38.

Figure 3:
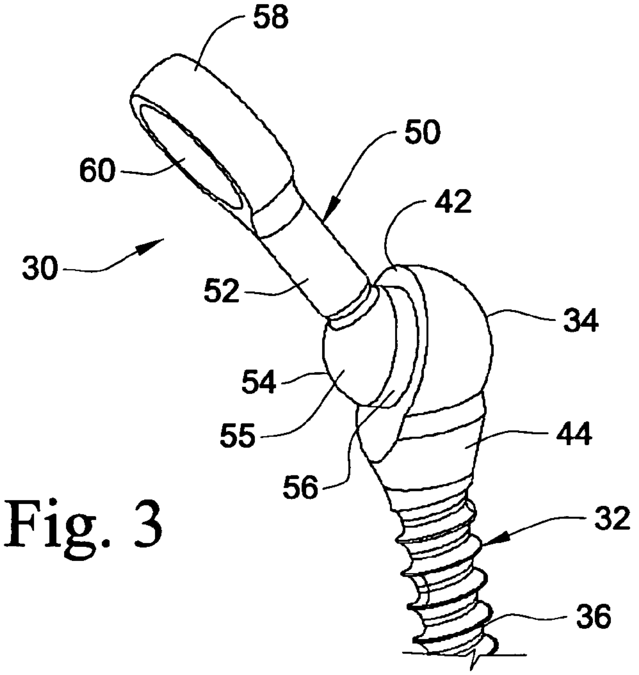
FIG. 3 is a perspective view of the assembly of FIG. 1 showing the connecting member entering the anchor in a first, unlocked orientation relative to the anchor.
Figure 4:
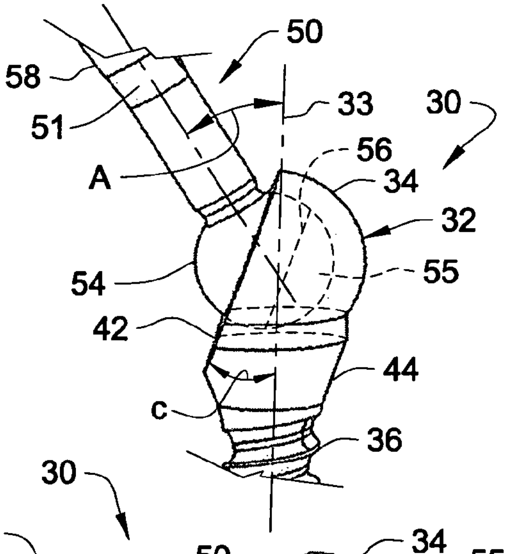
FIG. 4 is the view of the assembly of FIG. 1 with connecting member positioned in the anchor in the first orientation.

Stabilization system 30 can be assembled by inserting end member 55 into socket 40 of anchor 32. As shown in FIG. 3, connecting member 50 is oriented to align cut 56 with opening 38 of anchor 32. In one embodiment, the diameter of end member 55 at cut 56 is slightly less than the diameter of opening 38. This permits end member 55 to slide through opening 38 and into socket 40. End member 55 is slid into socket 40 with cut 56 maintained in alignment with opening 38 until end member 55 is seated in socket 40, as shown in FIG. 4. When seated in socket 40, connecting member 50 can pivot relative to anchor 32 since end member 55 can rotate in socket 40 to any one of an infinite number of second locked orientations, such as shown in FIG. 5, where cut 56 is not aligned with opening 38.

Connecting member 50 is maintained in engagement with anchor 32 since the dimensions of end member 55 at locations other than the portion circumscribed by cut 56 are greater than the maximum dimension of opening 38. Thus, when cut 56 is not aligned with opening 38, end member 55 cannot pass therethrough. Connecting member 50 can be disassembled from anchor 32 by aligning cut 56 with opening 38 and pulling connecting member 50 away from anchor 32 through opening 38.

When cut 56 is aligned with chamfered side 42 for entry into socket 40 through opening 38, as shown in FIG. 4, axis 51 is oriented at an angle A with longitudinal axis 33 of anchor 32. In the illustrated embodiment, angle A is about 30 degrees. In another embodiment, angle A can range from 0 degrees to 90 degrees. In a further embodiment, angle A can range from 15 degrees to 45 degrees, and in another embodiment angle A can range from 25 degrees to 35 degrees.

Figure 5:
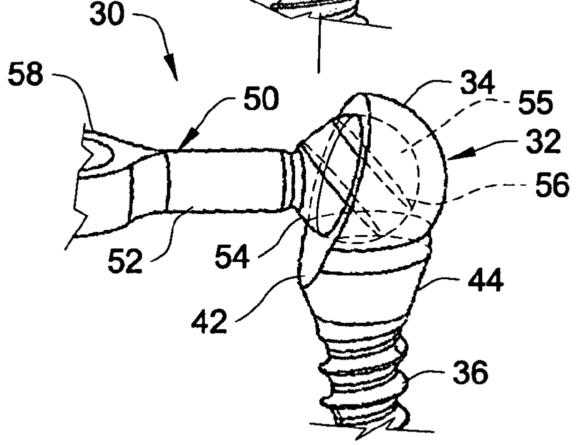
FIG. 5 is the view of the assembly of FIG. 1 with connecting member positioned in a second, locked orientation relative to the anchor.
Figure 6:
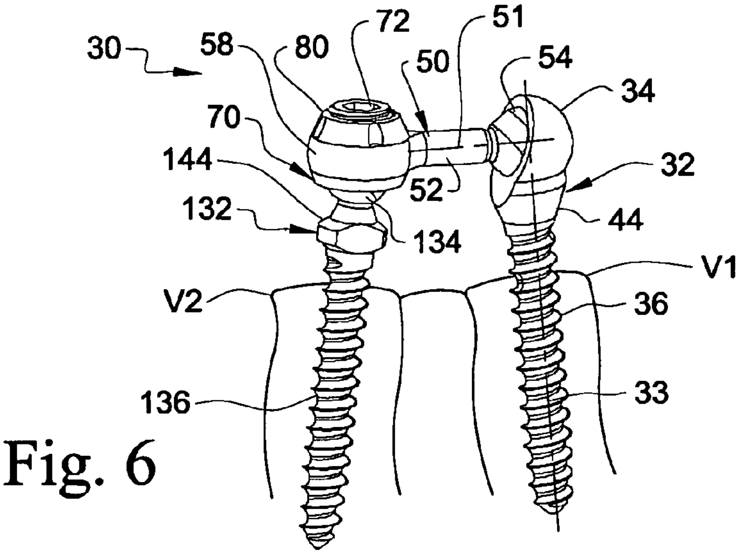
FIG. 6 is a perspective view of the assembly of FIG. 1 with the connecting member engaged to a second anchor and the anchors engaged to first and second vertebrae, the vertebrae shown diagrammatically.

Connecting member 50 can be pivoted from this initial insertion orientation to an orientation where second end 58 can be brought into alignment with a second anchor 132, as shown in FIGS. 5 and 6. Connecting member 50 can be pivoted to assume any one of an infinite number of positions relative to axis 33 of anchor 32. In the illustrated embodiment, the various orientations for connecting member 50 relative to anchor 32 are circumscribed by a cone having one side defined by angle A and an opposite side defined by locations where body 52 contacts chamfered side 42. This allows second end 58 to be engaged with second anchor 132 even if it is not aligned with opening 38 of anchor 32 and/or if anchor 132 does not project the same distance from vertebra V2 as anchor 32 projects from vertebra V1.

In FIG. 6, anchor 132 includes a bone engaging portion 136 engaged to a vertebral body V2 and anchor 32 includes bone engaging portion 36 engaged to vertebral body V1. Head 34 extends from vertebra V1 so that connecting member 50 can be received in socket 40 after anchor 32 is engaged to vertebra V1. Alternatively, connecting member 50 can be engaged to anchor 32 prior to engaging bone engaging portion 36 to vertebra V1. Anchor 132 includes a collar 144 between bone engaging portion 136 and a head 134, as shown in further detail in FIG. 7. Collar 144 includes a hex shape, and can be engaged by an insertion tool (not shown) positioned over head 134 to drive bone engaging portion 136 into vertebra V2 (or vertebra V1 in FIG. 7.) As discussed further below, head 134 includes a ball-shaped member with a circumferential cut 140, like end member 55 discussed above. A cap 70 can be engaged to head 134. Cap 70 includes a stem 72 extending proximally from head 134 about which second 58 of connecting member 50 can be positioned. A locking member 80 engages stem 70 to secure second end 58 to anchor 132. When assembled, connecting member 50 can pivot relative to each of the anchors 32, 132 to allow at least limited motion of the vertebral level along which connecting member 50 is engaged while body portion 52 maintains the spacing between the vertebrae V1, V2.

Other embodiments contemplate that the diameter of end member 55 can be the same as or slightly greater than the size of opening 38 of head 34. These embodiments further contemplate that connecting member 50 is pressed into socket 40 through opening 38 to overcome resistance encountered by contact with head 34. Other embodiments contemplate that one or both of end member 55 and socket 40 can be coated or lined with hard surface material, such as cobalt chrome or titanium carbide, for example. Still other embodiments contemplate that one or both of end member 55 and socket 40 can be coated or lined with non-metallic material that is softer than the material comprising end member 55 and/or head 34. Examples of such non-metallic material include Teflon, polyethylene, peek, or other plastic or polymer material.

Figure 7:
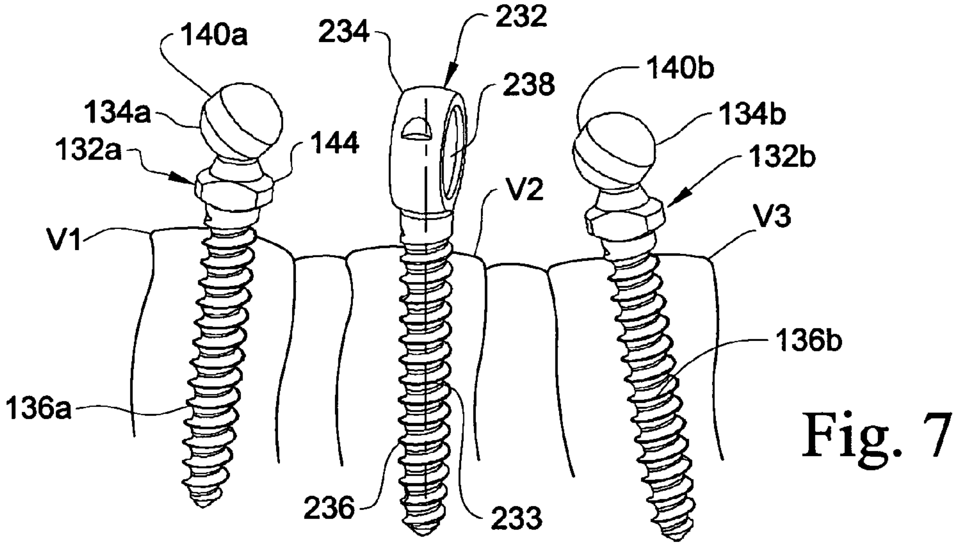
FIG. 7 is a perspective view of first and second anchors with an intermediate anchor therebetween arranged to receive a connecting member assembly and the anchors engaged to respective ones of three vertebrae, the vertebrae shown diagrammatically.

Another embodiment stabilization system contemplates application in multi-level spinal stabilization procedures involving three or more vertebrae, as shown in FIG. 7. In FIG. 7, anchor **132*a* is engaged to vertebra V1 and anchor 132*b* is engaged to vertebra V3. An intermediate anchor 232 is engaged to vertebra V2 situated between vertebrae V1 and V3. Intermediate anchor 232 includes a bone engaging portion 236 extending along longitudinal axis 233, and a head 234 at a proximal end of bone engaging portion 236. Head 234 is in the form of a ring having a central passage 238 extending therethrough transversely to longitudinal axis 233. Anchor 232 is engaged to vertebra V2 so that passage 238 is generally oriented toward anchors 132*a*, 132*b***.

Figure 8:
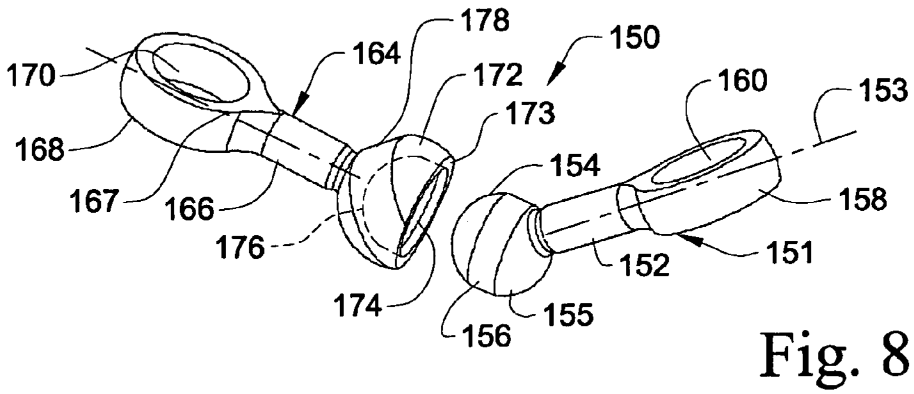
FIG. 8 is an exploded perspective view of another embodiment connecting member assembly engageable to the anchors of FIG. 7.

FIG. 8 shows another embodiment connecting member assembly 150 engageable to anchors **132*a*, 232, 132*b* for a multi-level spinal stabilization procedure. Connecting member assembly 150 includes a first connecting portion 151 along longitudinal axis 153 that is substantially similar to connecting member 50 discussed above. First connecting portion 151 includes an elongated body portion 152 extending between a first end 154 and a second end 158. First end 154 includes a ball-shaped end member 155 having a circumferential cut 156 extending therearound. Second end 158 includes a ring-shaped member with a passage 160 extending therethrough transversely to longitudinal axis 153**.

Connecting member assembly 150 further includes a second connecting portion 164 removably engageable with first connecting portion 151 to form a multi-level articulating stabilization construct. Second connecting portion 164 extends along longitudinal axis 167 between a first end 172 and a second end 168. Second end 168 includes a ring-shaped member with a passage 170 extending therethrough transversely to longitudinal axis 167. First end 172 includes an enlarged end member in the form of a hemi-sphere defining a socket 176 therein. The flat end wall 173 of the hemi-spherical shape includes an end opening 174 that opens along axis 167 in end wall 173. End opening 174 is in communication with socket 176, and is located so that socket 176 includes a maximum dimension within the end member that is slightly larger than the dimension of end opening 174. First end 172 further includes a cut 178 extending thereabout from one side of end wall 173 to the opposite side.

Figure 9:
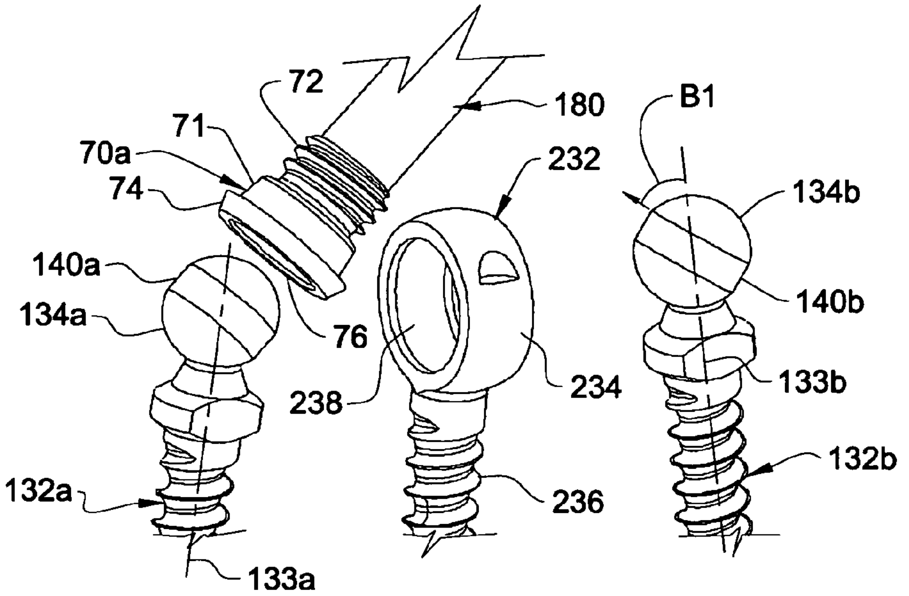
FIG. 9 is a perspective view of proximal portions of the anchors of FIG. 7 with a cap oriented for positioning on a head of the first anchor.

One procedure for assembling connecting member assembly 150 to anchors **132*a*, 232, 132*b* will now be discussed with reference to FIGS. 9-19. In FIG. 9, cap 70*a* is loaded on a distal end of insertion tool 180. Cap 70*a* includes a body 71 having a proximal stem 72 and a distal flange 74 radially outwardly from body 71 about stem 72. At least a proximal end of stem 72 is threaded for engagement with a locking member 80. Body 71 further defines an internal socket that opens distally at opening 76**.

Anchors **132*a*, 132*b* each include a ball-shaped head 134*a*, 134*b* with cut 140*a*, 140*b* therearound. Cut 140*a*, 140*b* is angled at angle B1 relative to the longitudinal axis 133*a*, 133*b* of the respective anchor 132*a*, 132*b*, and head 134*a*, 134*b* is sized relative to opening 76 to permit passage of head 134*a*, 134*b* through opening 76 when cut 140*a*, 140*b* is aligned therewith, as shown in FIG. 9. In the illustrated embodiment, angle B1 is about 45 degrees. In another embodiment, angle B1 can range from 0 degrees to 90 degrees. Angle B1 can range from 30 degrees to 60 degrees in another embodiment. Angle B1** can range from 40 degrees to 50 degrees in yet another embodiment.

Figure 10:
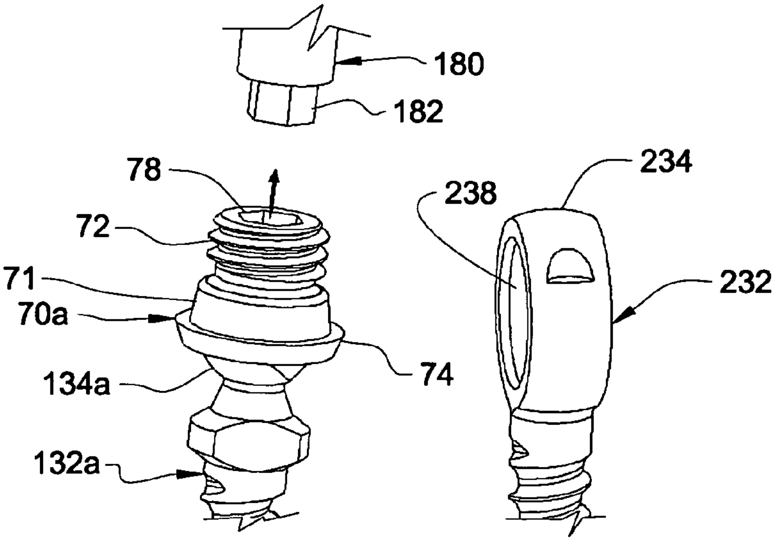
FIG. 10 is a perspective view of the proximal portions of the first anchor and the intermediate anchor of FIG. 9 with the cap positioned on the head of the first anchor.

As shown in FIG. 10, after placing cap 70 over head 134*a* along cut 140*a*, cap 70*a* can be pivoted so that stem 72 aligns generally with the longitudinal axis 133*a* of anchor 132*a*. Cap 70*a* is pivotally captured on head 134*a* since the diameter of head 134*a* at locations other than cut 140*a* is greater then the diameter of opening 76, similar to the coupling arrangement discussed above for connecting member 50 and anchor 32. Insertion tool 180 can then be withdrawn so that engaging end 182 is withdrawn from tool engaging bore 78 of cap 70*a*. In another embodiment, cap 70*a* can be pre-assembled with anchor 134*a*, and the entire assembly can be engaged simultaneously to the respective vertebra.

Figure 11:
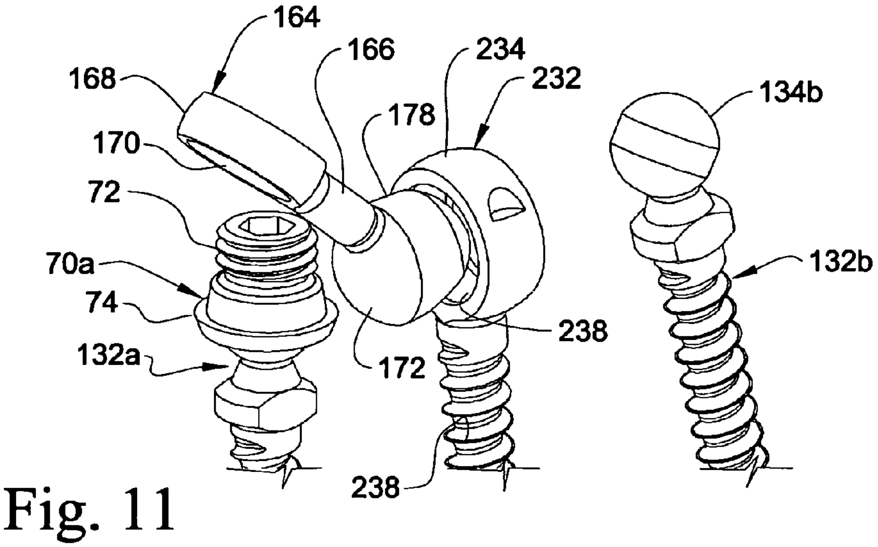
FIG. 11 is a perspective view of proximal portions of the anchors of FIG. 7 with the cap engaged to the first anchor and a first portion of the connecting member assembly of FIG. 8 oriented for engagement with the intermediate anchor.
Figure 12:
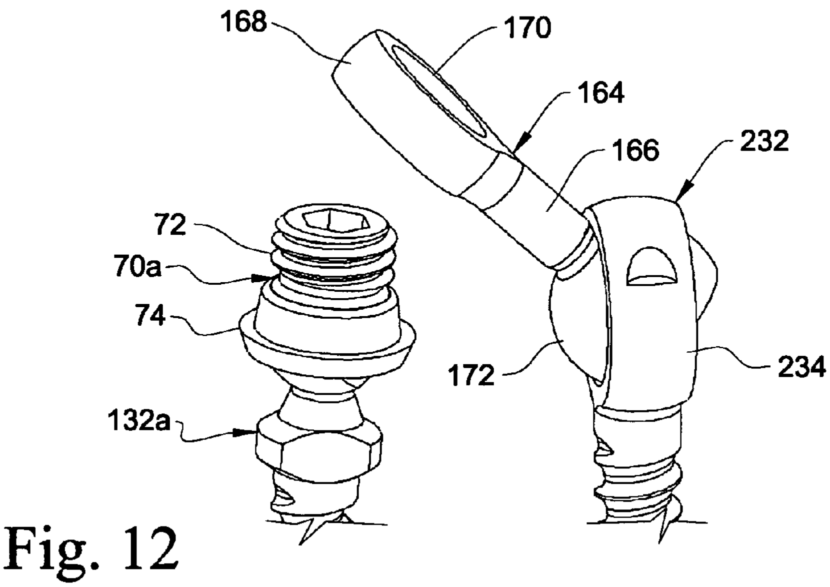
FIG. 12 is a perspective view of the first anchor and intermediate anchor of FIG. 11 with the first connecting portion positioned in the intermediate anchor in an unlocked orientation.
Figure 13:
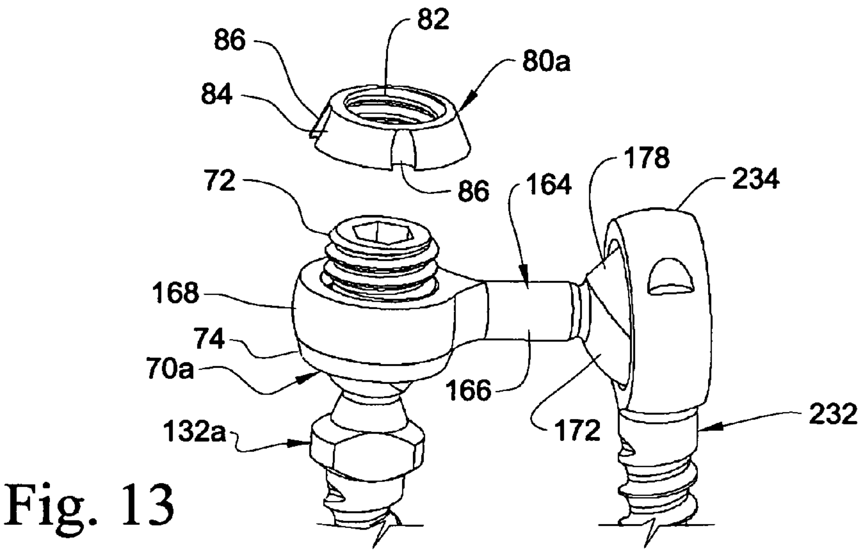
FIG. 13 is a perspective view of the first anchor and the intermediate anchor of FIG. 12 with the first connecting portion in a locked orientation relative to the intermediate anchor and the opposite end of the first connecting portion positioned about the cap of the first anchor and the locking member positioned for engagement with the cap on the first anchor.
Figure 14:
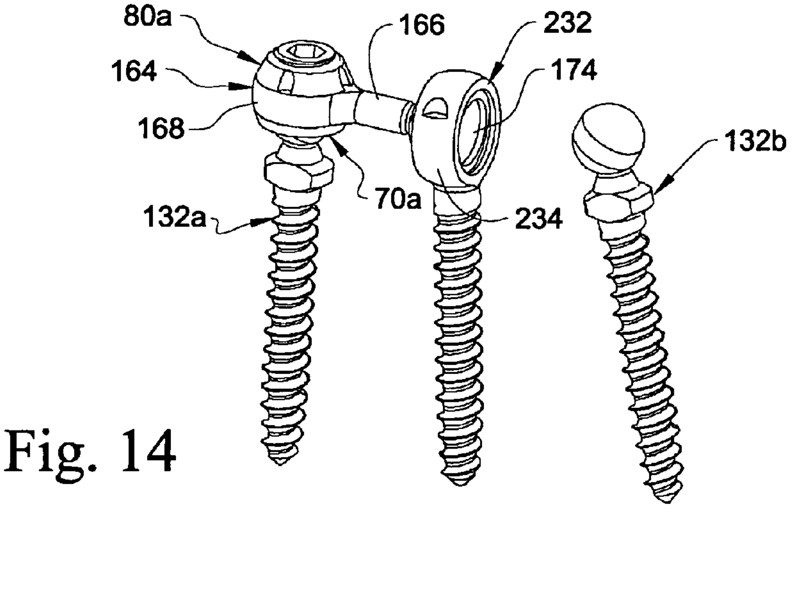
FIG. 14 is a perspective view of the anchors of FIG. 7 showing the first connecting portion engaged to the first and intermediate anchors and the locking member engaged to the cap of the first anchor.

Second connecting portion 164 of connecting member assembly 150 can now be assembled between anchors 132*a*, 232, as shown in FIGS. 11-14. First end 172 is oriented so that cut 178 is aligned with the opening into passage 238, as shown in FIG. 11. First end 172 is then advanced into passage 238 until cut 178 is aligned with the ring-like member defining head 234, as shown in FIG. 12. Second end 168 can then be pivoted relative to intermediate anchor 232 and positioned about stem 72 of cap 70*a*, as shown in FIG. 13. In this pivoted position, first end 172 is locked in head 234 since the opening into passage 238 is sized smaller than the maximum dimension of passage 238, and the dimensions of first end 172 at locations other than at cut 178 prevent end member 172 from being withdrawn through the opening to passage 238. Opening 174 is oriented toward anchor 132*b* for receipt of first connecting portion 151, as shown in FIG. 14 and as discussed further below.

A lock member 80*a* can be engaged about stem 72 and threadingly engaged thereto to secure second end 168 of connecting portion 164 to cap 70*a* and thus to anchor 132*a*, as shown in FIG. 14. In then illustrated embodiment, lock member 80*a* is in the form of an internally threaded nut with a bore 82 and sidewalls 84. Sidewalls 84 can be tapered to extend outwardly for alignment with the outer perimeter of second 168 of connecting portion 164. Sidewalls 84 can include recesses 86 to provide engagement platforms for a tool to engage lock member 80*a* to apply sufficient force to secure it to connecting portion 164 and cap 70*a*.

Figure 15:
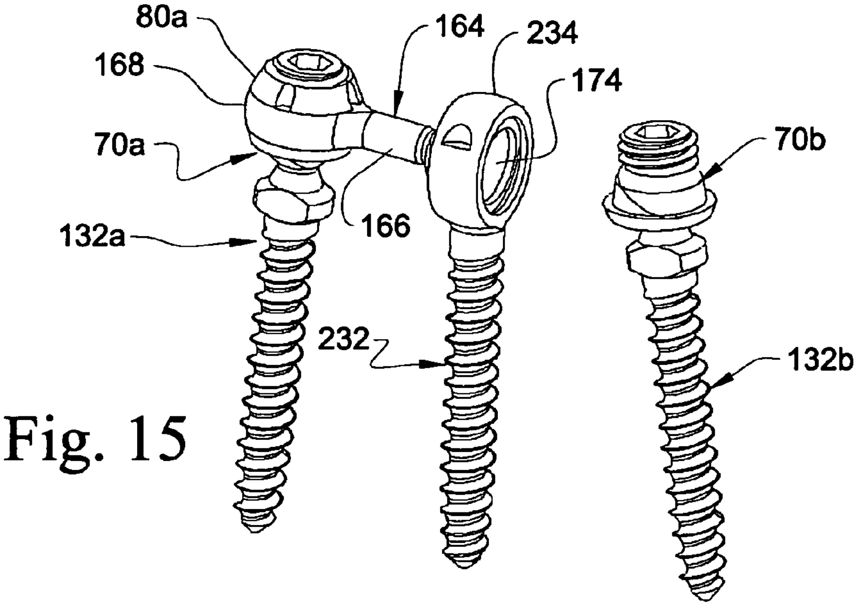
FIG. 15 is the view of FIG. 14 showing a cap engaged to the third anchor.
Figure 16:
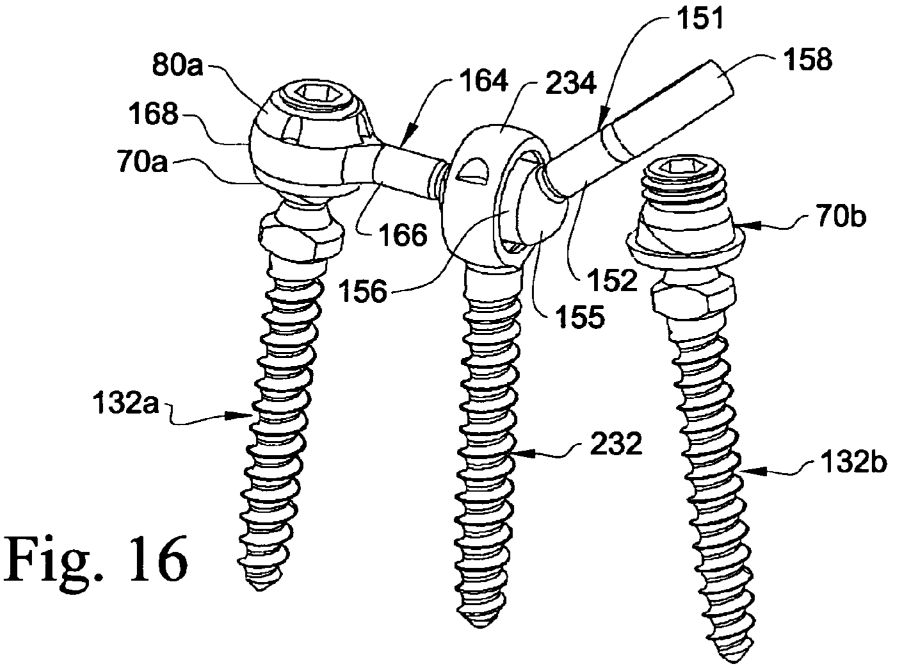
FIG. 16 is the view of FIG. 15 showing a second connecting portion of the connecting member assembly with the second connecting portion positioned in a first, unlocked orientation relative to the first connecting portion.
Figure 17:
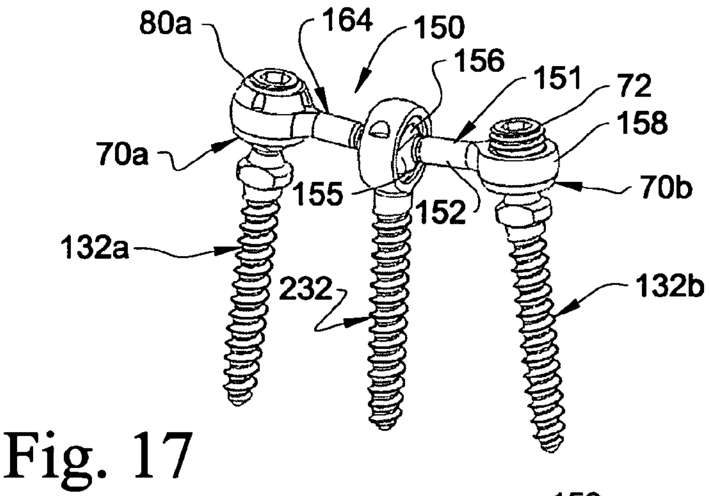
FIG. 17 is the view of FIG. 16 showing the second connecting portion in a second, locked orientation relative to the first connecting portion and positioned about the cap on the third anchor.
Figure 18:
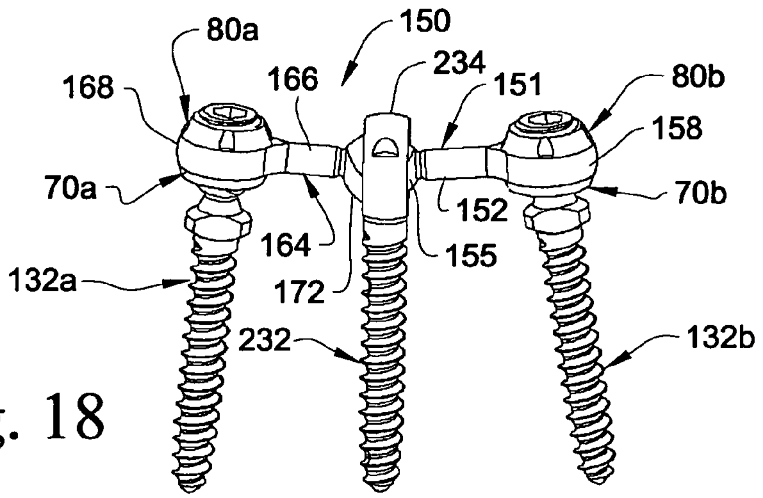
FIG. 18 is a perspective view showing the connecting member assembly of FIG. 8 engaged to the anchors of FIG. 7.

In FIG. 15, a second cap 70*b* is installed or pre-installed on anchor 132*b* in a manner similar to that discussed above with respect to cap 70*a* installed on anchor 132*a*. Connecting portion 151 is then positioned with cut 156 on end member 155 aligned with opening 174 of second connecting portion 164, as shown in FIG. 16. End member 155 is then advanced through opening 174 in this orientation and into socket 176 until cut 156 passes through opening 174. Connecting portion 151 can then be pivoted about end member 155 in socket 176 to position second end 158 about stem 72 of cap 70*b*, as shown in FIG. 17. This orients cut 156 out of alignment with opening 174, capturing end member 155 in socket 176 of connecting portion 164. A second lock member 80*b* can then be engaged to second cap 70*b*, as shown in FIG. 18, to secure connecting portion 151 to anchor 132*b*. The assembled construct of FIG. 18 provides a multi-level stabilization construct that allows each of the connecting portions 151, 164 to articulate about its connection with each of the anchors 132*a*, 232, 132*b* and also about the connection between connecting portions 151, 164. The longitudinal axes 153, 167 of connecting portions 151, 164 intersect in passage 238, minimizing the profile of the construct projecting from the vertebrae.

Figure 19:
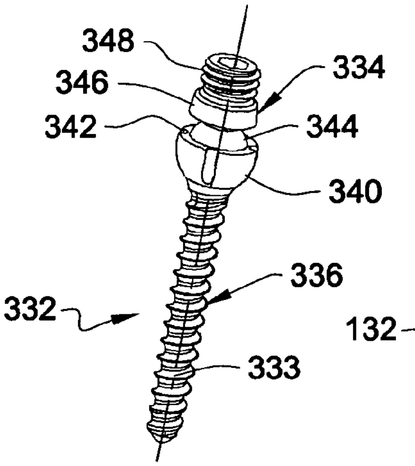
FIG. 19 is a perspective view of another embodiment anchor and cap assembly.

Referring now to FIG. 19, another embodiment anchor 332 is shown. Anchor 332 includes a head 334 and a distal bone engaging portion bone engaging portion 336 extending along a longitudinal axis 333. A collar 340 is located at a proximal end of bone engaging portion 336. Collar 340 includes an axially oriented and proximally opening socket 342. Head 334 includes a distal end member 344 pivotally received in socket 342. Head 334 further includes a flange portion 346 to support an end of a connecting member or connecting portion thereon, and a threaded stem 348 to receive a locking member 80 to secure the connecting member or connecting portion thereto. End member 344 can be configured like the end members of the connecting member and connecting portions discussed above, and can be a ball-shaped member that includes a cut extending therearound sized to permit insertion through the opening into socket 342 in a first orientation. The dimensions of the ball-shaped member at locations other than the cut are sized to capture end member 344 in socket 342 when pivoted in the socket 342 from the insertion orientation.

Figure 20:
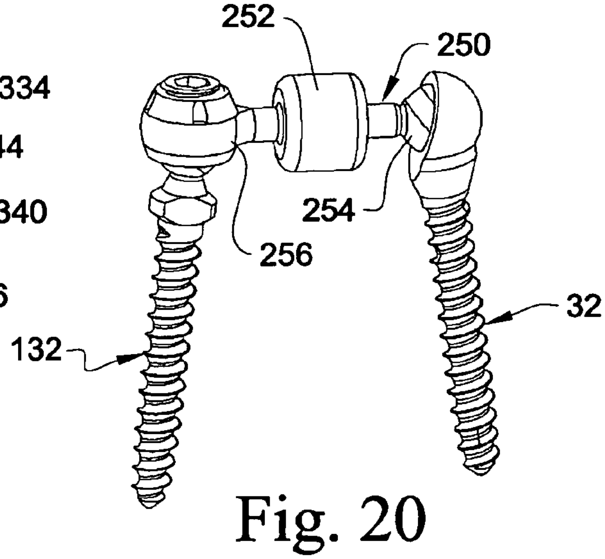
FIG. 20 is a perspective view of another embodiment connecting member assembly engaged between a pair of anchors.

FIG. 20 shows another embodiment connecting member 250 positionable between and engageable to anchors 32, 132 with ends 254, 256 in a manner like that discussed above with respect to connecting member 50. Connecting member 250 includes a flexible intermediate portion 252 between ends 254, 256. Intermediate portion 252 can compress to allow the spacing between the vertebrae to be variable, and also to provide additional bending and lateral motion capabilities for the stabilized vertebrae. Such a flexible intermediate portion could also be employed in or both of the portions of a multi-level stabilization construct such as connecting member 150.

The anchors discussed herein include bone engaging portions for engagement with the respective vertebral structure. In the illustrated embodiments, the bone engaging portions are a bone screw with a threaded shank to engage the bony structure of the underlying vertebrae. The bone engaging portion can be pivotally received or engaged to the head of the anchor to provide a multi-axial arrangement, or can be fixed relative thereto to provide a uni-axial arrangement. The bone engaging portion can be in the form of a spike, staple, fusion device, cannulated screw, fenestrated screw, interbody device, intrabody device, clamp, plate, suture anchor, bolt, pin or other bone engaging member.

Various surgical techniques can be completed with the systems discussed herein. One type of surgical technique is directed to spinal surgery for positioning an elongated connecting element along one or more vertebral levels to provide spinal stabilization. A number of anchors are selected according to the number of vertebral levels to be instrumented. For example, a single level procedure may include an anchor engaged to each of two adjacent vertebrae, or a two level procedure may include an anchor engaged to each of three adjacent vertebrae.

When the desired number of levels for stabilization has been selected, the anchors can be engaged to the respective vertebrae. In posterior spinal surgical techniques, the anchors can be screws engaged in the pedicles of the vertebrae. The anchors can be positioned into the patient through one or more minimally invasive access portals, formed by an incision, cannula, or retractor system, for example. Placement of the anchors can be facilitated using a guidewire, image guided surgery system, fluoroscopic imaging, X-rays, CT scans, endoscopic viewing systems, microscopic viewing systems, loupes, and/or naked eye visualization, for example. With the anchors engaged to the vertebrae, the connecting member or connecting portions can be assembled to the anchors as discussed above.

One or more other connecting members can be similarly engaged to the spinal column along the same vertebral level or levels, or along other vertebral levels. Other procedures can also be completed in conjunction with the stabilization procedure, including discectomy, interbody fusion, artificial disc replacement, bone removal, tissue removal, intravertebral reduction, joint replacement, annular repair, and/or any other spinal surgical procedures. In multi-level stabilization procedures, one level can be fused, and the fused level and the next adjacent superior level can be stabilized with the multi-level stabilization system herein.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A system for stabilization of a spinal column segment, comprising:

an elongate member extending between a first end and a second end, said first end including a ball-shaped member having a circumferential cut and a connecting portion extending from said first end to a second end, said second end including an anchor engaging member defining a passage;

a first anchor including a distal bone engaging portion extending on a longitudinal axis and a proximal head, said head including a bulbous shape with a chamfered surface defining a plane on one side of the head that is acutely angled with said longitudinal axis, the head further including an opening in said plane surrounded by said chamfered surface so that said opening lies in said plane and extends through said chamfered surface into a spherical socket defined by said head, said socket having a first maximum dimension and said opening into said socket having a second maximum dimension that is less than said first maximum dimension, wherein said cut is sized to pass through said opening when aligned therewith and said ball-shaped member is sized greater than said second maximum dimension to prevent said ball-shaped member from passing through said opening of said socket when said cut is not aligned with said opening, wherein said first anchor includes a collar that extends from said bone engaging portion to said head and said chamfered surface has a proximal end aligned with said longitudinal axis and extends in said plane through said collar to a distal end of said chamfered surface that is offset to one side of said longitudinal axis, said chamfered surface forming an acute angle with said longitudinal axis from said proximal end of said chamfered surface to said distal end of said chamfered surface; and a second anchor including a distal bone engaging portion and a proximal portion, said second anchor further including a stem pivotally coupled to said proximal portion and extending proximally from said bone engaging portion, said stem being positionable in said passage of said anchor engaging member of said elongate member for engagement thereto.

2. The system of claim 1, further comprising a locking member engageable about said stem to secure said second end of said elongate member to said second anchor.

3. The system of claim 2, wherein said proximal portion of said second anchor includes a second ball-shaped member defining a circumferential cut, said proximal portion of said second anchor further including a second socket pivotally connecting second ball-shaped member therein with said stem extending proximally from said pivotal connection.

4. The system of claim 3, wherein said second socket includes a first maximum dimension and an opening into said second socket includes a second maximum dimension less than said first maximum dimension, wherein said cut of said second ball-shaped member is sized to pass through said opening into said second socket when said cut is aligned therewith, said second ball-shaped member further including a size greater than said second maximum dimension to prevent said second ball-shaped member from passing through said opening of said second socket when said cut of said second ball-shaped member is not aligned with said opening of said second socket.

5. The system of claim 4, wherein said second ball-shaped member is integral with said bone engaging portion of said second anchor at a proximal end thereof and said second socket is defined by a distal portion of a cap positionable about said second ball-shaped member, said stem extending proximally from said distal portion of said cap.

6. The system of claim 4, wherein said second socket is integral with said bone engaging portion of said second anchor at a proximal end thereof and said second ball-shaped member is defined by a distal portion of a cap positionable within said second socket, said stem extending proximally from said distal portion of said cap.

7. The system of claim 1, wherein said elongate member includes a flexible intermediate portion between said first and second ends.

8. The system of claim 1, wherein said second anchor includes a collar between said bone engaging portion and a head at said proximal portion of said second anchor, wherein said collar includes an outer hexagonal shape to receive a driving instrument positioned around said head.

9. The system of claim 8, wherein said head of said second anchor includes a ball-shaped member with a circumferential cut extending therearound.

10. The system of claim 1, wherein said stem is threaded and received in said passage of said anchor engaging member of said elongate member, and further comprising a locking member engaged about said stem to secure said anchor engaging member of said elongate member to said second anchor with said elongate member pivotal relative to said first and second anchors while said elongate member is engaged to said first and second anchors.

11. A method for assembling a spinal stabilization system, comprising:

providing a first anchor including a bone engaging portion extending on a longitudinal axis and a proximal head, the head including a bulbous shape defining a spherical socket therein and a chamfered surface defining a plane on one side of the head that is acutely angled with said longitudinal axis, the head further including an opening in said plane that is surrounded by said chamfered surface so that said opening lies in said plane and extends through the chamfered surface and into the socket of the head, wherein the first anchor includes a collar that extends from the bone engaging portion to the head and the chamfered surface has a proximal end aligned with the longitudinal axis and extends in the plane through the collar to a distal end of the chamfered surface that is offset to one side of the longitudinal axis, the chamfered surface forming an acute angle with the longitudinal axis from the proximal end of the chamfered surface to the distal end of the chamfered surface;

providing an elongate connecting member having a ball-shaped member at one end thereof, the ball-shaped member defining a circumferential cut extending there-around;

aligning the circumferential cut with the opening into the socket;

inserting the ball-shaped member through the opening and into the socket in the aligned orientation; and pivoting the ball-shaped member in the socket so that the cut is not aligned with the opening, wherein the ball-shaped member is sized to prevent the ball-shaped member from passing through the opening when the cut is not aligned with the opening.

12. The method of claim 11, further comprising:

providing a second anchor including a distal bone engaging portion and a proximal cap pivotal relative to the bone engaging portion, the cap including a proximally extending stem;

positioning a second end of the connecting member about the stem; and engaging a locking member to the stem to secure the second end of the connecting member to the cap while the connecting member remains pivotal relative to the second anchor.

13. A system for stabilization of a spinal column segment. comprising:

an elongate member extending between a first end and a second end, said first end including a ball-shaped member having a circumferential cut and a connecting portion extending from said first end to a second end, said second end including an anchor engaging member defining a passage;

a first anchor including a distal bone engaging portion extending on a longitudinal axis and a proximal head, wherein said first anchor includes a collar that extends from said bone engaging portion to said head with said head including a bulbous shape with a chamfered surface on one side of said head that is obliquely angled to said longitudinal axis and said chamfered surface surrounds and defines an oblique opening into a spherical socket within said head, said chamfered surface having a proximal end aligned with said longitudinal axis and said chamfered surface extends distally from said proximal end to lie in a plane forming an acute angle to said longitudinal axis, said chamfered surface extending in said plane through said collar to a distal end of said chamfered surface that is offset to one side of said longitudinal axis, wherein said socket has a first maximum dimension and said opening into said socket having a second maximum dimension that is less than said first maximum dimension, wherein said cut is sized to pass through said opening when aligned therewith and said ball-shaped member is sized greater than said second maximum dimension to prevent said ball-shaped member from passing through said opening of said socket when said cut is not aligned with said opening; and a second anchor including a distal bone engaging portion and a proximal portion, said second anchor further including a stem pivotally coupled to said proximal portion and extending proximally from said bone engaging portion, said stem being positionable in said passage of said anchor engaging member of said elongate member for engagement thereto.

14. The system of claim 13, wherein said proximal portion of said second anchor includes a second ball-shaped member defining a circumferential cut, said proximal portion of said second anchor further including a second socket pivotally connecting second ball-shaped member therein with said stem extending proximally from said pivotal connection, and further comprising further comprising a locking member engageable about said stem to secure said engaging member of said elongate member to said second anchor.

15. The system of claim 14, wherein said second socket includes a first maximum dimension and an opening into said second socket includes a second maximum dimension less than said first maximum dimension, wherein said cut of said second ball-shaped member is sized to pass through said opening into said second socket when said cut is aligned therewith, said second ball-shaped member further including a size greater than said second maximum dimension to prevent said second ball-shaped member from passing through said opening of said second socket when said cut of said second ball-shaped member is not aligned with said opening of said second socket.

16. The system of claim 15, wherein said second ball-shaped member is integral with said bone engaging portion of said second anchor at a proximal end thereof and said second socket is defined by a distal portion of a cap positionable about said second ball-shaped member, said stem extending proximally from said distal portion of said cap.

17. The system of claim 15, wherein said second socket is integral with said bone engaging portion of said second anchor at a proximal end thereof and said second ball-shaped member is defined by a distal portion of a cap positionable within said second socket, said stem extending proximally from said distal portion of said cap.

18. The system of claim 13, wherein:

said collar distally tapers from said head to said bone engaging portion; and said second anchor includes a collar between said bone engaging portion and said proximal portion, wherein said collar includes a hexagonal shape to receive a driving instrument positioned around said head.

* * * * *